(12) United States Patent
Chin et al.

(10) Patent No.: US 10,076,369 B2
(45) Date of Patent: Sep. 18, 2018

(54) BONE FASTENER FOR A SPINAL FIXATION ASSEMBLY

(71) Applicants: Kingsley R. Chin, Wilton Manors, FL (US); Lin Yin, Brookline, MA (US); Jacob R. Lubinski, Beverly, MA (US)

(72) Inventors: Kingsley R. Chin, Wilton Manors, FL (US); Lin Yin, Brookline, MA (US); Jacob R. Lubinski, Beverly, MA (US)

(73) Assignee: SPINEFRONTIER, INC, Malden, MA (US)

( * ) Notice: Subject to any disclaimer, the term of this patent is extended or adjusted under 35 U.S.C. 154(b) by 563 days.

(21) Appl. No.: 14/636,884

(22) Filed: Mar. 3, 2015

(65) Prior Publication Data

US 2015/0216573 A1 Aug. 6, 2015

Related U.S. Application Data

(63) Continuation-in-part of application No. 13/742,898, filed on Jan. 16, 2013, now abandoned.
(Continued)

(51) Int. Cl.
*A61B 17/80* (2006.01)
*A61B 17/84* (2006.01)
(Continued)

(52) U.S. Cl.
CPC ...... *A61B 17/8052* (2013.01); *A61B 17/7059* (2013.01); *A61B 17/8047* (2013.01); *A61B 17/844* (2013.01); *A61B 17/8615* (2013.01); *A61F 2/4425* (2013.01); *A61F 2/4455* (2013.01); *A61B 17/8009* (2013.01); *A61B 17/8042* (2013.01); *A61F 2002/3052* (2013.01); *A61F 2002/3055* (2013.01); *A61F 2002/30387* (2013.01); *A61F 2002/30471* (2013.01);
(Continued)

(58) Field of Classification Search
CPC . A61B 17/80; A61B 17/8052; A61B 17/8057; A61B 17/84; A61B 17/17; A61B 17/7059
See application file for complete search history.

(56) References Cited

U.S. PATENT DOCUMENTS

| 5,275,601 A | 1/1994 | Gogolewski et al. |
| 5,425,733 A | 6/1995 | Schmieding |

(Continued)

FOREIGN PATENT DOCUMENTS

| DE | 4409833 | 10/1995 |
| WO | WO2006133086 A2 | 12/2006 |

(Continued)

*Primary Examiner* — Christopher Beccia
(74) *Attorney, Agent, or Firm* — AKC Patents, LLC

(57) ABSTRACT

An implantable cervical plate assembly includes a cervical plate, one or more bone fasteners. The cervical plate comprises an elongated asymmetric body having one or more through-openings extending from the front surface to the back surface of the elongated asymmetric body. The one or more bone fasteners are configured to be inserted through the one or more through-openings, respectively. The bone fasteners comprise a threaded main body and a head that includes one or more breakable structures configured to be broken when inserted into a groove and then unflex and remain captured within the groove.

20 Claims, 20 Drawing Sheets

Related U.S. Application Data

(60) Provisional application No. 61/947,605, filed on Mar. 4, 2014.

(51) Int. Cl.
   *A61B 17/86* (2006.01)
   *A61B 17/70* (2006.01)
   *A61F 2/44* (2006.01)
   *A61F 2/30* (2006.01)

(52) U.S. Cl.
   CPC ............... *A61F 2002/30481* (2013.01); *A61F 2002/30482* (2013.01); *A61F 2002/30507* (2013.01); *A61F 2002/30538* (2013.01); *A61F 2002/30578* (2013.01); *A61F 2002/30624* (2013.01); *A61F 2002/30787* (2013.01)

(56) References Cited

U.S. PATENT DOCUMENTS

| | | |
|---|---|---|
| 5,662,652 A | 9/1997 | Schafer et al. |
| 6,030,389 A | 2/2000 | Wagner et al. |
| 6,286,401 B1 | 9/2001 | Hajianpour |
| 6,331,179 B1 | 12/2001 | Freid et al. |
| 6,454,769 B2 | 9/2002 | Wagner et al. |
| 6,461,359 B1 | 10/2002 | Tribus et al. |
| 6,623,485 B2 | 9/2003 | Doubler et al. |
| 6,730,127 B2 | 5/2004 | Michelson |
| 6,964,664 B2 | 11/2005 | Freid et al. |
| 7,112,222 B2 | 9/2006 | Fraser et al. |
| 7,255,699 B2 * | 8/2007 | Paul ................... A61B 17/7059 606/250 |
| 7,303,564 B2 | 12/2007 | Freid et al. |
| 7,309,340 B2 | 12/2007 | Fallin et al. |
| 7,341,589 B2 | 3/2008 | Weaver et al. |
| 7,594,931 B2 | 9/2009 | Louis et al. |
| 7,628,816 B2 | 12/2009 | Magerl et al. |
| 7,819,903 B2 | 10/2010 | Fraser et al. |
| 7,963,982 B2 | 6/2011 | Kirschman |
| 2004/0019353 A1 | 1/2004 | Freid et al. |
| 2004/0068319 A1 | 4/2004 | Cordaro |
| 2004/0097935 A1 | 5/2004 | Richelsoph et al. |
| 2004/0210218 A1 | 10/2004 | Dixon et al. |
| 2004/0225292 A1 | 11/2004 | Sasso et al. |
| 2005/0192578 A1 | 9/2005 | Horst |
| 2006/0036249 A1 * | 2/2006 | Baynham ............ A61B 17/7059 606/247 |
| 2006/0149253 A1 | 7/2006 | Doubler et al. |
| 2006/0229620 A1 | 10/2006 | Rothman et al. |
| 2006/0235518 A1 | 10/2006 | Blain |
| 2006/0276793 A1 * | 12/2006 | Berry ................ A61B 17/8052 606/70 |
| 2007/0055252 A1 | 3/2007 | Blain et al. |
| 2007/0162019 A1 | 7/2007 | Burns et al. |
| 2008/0021476 A1 | 1/2008 | Kirschman |
| 2008/0097444 A1 * | 4/2008 | Erickson ............ A61B 17/8052 606/281 |
| 2008/0177263 A1 | 7/2008 | Freedman et al. |
| 2008/0288001 A1 | 11/2008 | Cawley et al. |
| 2008/0294262 A1 | 11/2008 | Levieux |
| 2008/0306550 A1 | 12/2008 | Matityahu |
| 2009/0024170 A1 * | 1/2009 | Kirschman ........ A61B 17/8052 606/280 |
| 2009/0270926 A1 | 10/2009 | Hawkes et al. |
| 2009/0270927 A1 * | 10/2009 | Perrow ............... A61B 17/7059 606/286 |
| 2009/0287257 A1 | 11/2009 | Hagen |
| 2009/0326580 A1 | 12/2009 | Anderson et al. |
| 2010/0042160 A1 | 2/2010 | Biyani et al. |
| 2010/0106196 A1 * | 4/2010 | Erickson ........... A61B 17/1728 606/281 |
| 2010/0211116 A1 | 8/2010 | Suh et al. |
| 2010/0249937 A1 | 9/2010 | Blain et al. |
| 2011/0004253 A1 | 1/2011 | Fraser et al. |
| 2011/0015745 A1 | 1/2011 | Bucci |
| 2011/0082506 A1 | 4/2011 | Lore et al. |
| 2011/0087327 A1 | 4/2011 | Lechmann et al. |
| 2013/0184749 A1 | 7/2013 | Lore et al. |

FOREIGN PATENT DOCUMENTS

| | | |
|---|---|---|
| WO | 2007090017 A1 | 8/2007 |
| WO | WO2008021656 A2 | 2/2008 |
| WO | 2008123879 A1 | 10/2008 |

* cited by examiner

BONE FASTENER FOR A SPINAL FIXATION ASSEMBLY

CROSS REFERENCE TO RELATED CO-PENDING APPLICATIONS

This application claims the benefit of U.S. provisional application Ser. No. 61/947,605 filed Mar. 4, 2014 and entitled "BONE FASTENER FOR A SPINAL FIXATION ASSEMBLY", the contents of which are expressly incorporated herein by reference.

This application is also a continuation in part and claims the benefit of U.S. application Ser. No. 13/742,898 filed Jan. 16, 2013 and entitled "SYSTEM AND METHOD FOR A SPINAL STABILIZATION IMPLANT ASSEMBLY", the contents of which are expressly incorporated herein by reference.

FIELD OF THE INVENTION

The present invention relates to a bone fastener used for attaching a spinal plate to vertebral elements, and in particular to a bone fastener with breakable head components.

BACKGROUND OF THE INVENTION

Spine fixation assemblies are used to stabilize diseased or surgically removed vertebral elements. Several prior art spine fixation assemblies utilize rods and/or plates as connecting and stabilization elements between the vertebral elements. The rods and/or plates are usually secured to vertebral bones with screws. In situations and/or spinal locations where the vertebral elements are allowed to move after the rod or plate is attached, stresses associated with this motion or stresses due the motion of adjacent vertebral elements often cause the screws to disengage from the rod or plate and finally from the vertebral elements. Accordingly, there is a need for a locking mechanism that would prevent such a disengagement of the screws from the rod or plate and the vertebral elements.

SUMMARY OF THE INVENTION

The present invention relates to a system and method for a bone fastener used for securing a spinal plate assembly to vertebral elements. The bone fastener includes a self-contained locking mechanism that prevents accidental disengagement of the bone fastener due to stresses after they have been attached to the vertebral elements. The bone fastener comprises a threaded main body and a head. The threaded main body comprises threads for engaging a spinal vertebra and the head comprises one or more breakable structures configured to break when inserted into an opening of the spinal plate.

In general, in one aspect, the invention features an implantable cervical plate assembly for stabilization of two adjacent spinal vertebras, including a cervical plate and two or more bone fasteners. The cervical plate includes an elongated body having two or more through-openings extending from a front surface to a back surface of the elongated body. The two or more bone fasteners are configured to be inserted through the two or more through-openings, respectively, and to be attached to two or more locations in the two adjacent spinal vertebras, respectively, thereby attaching the cervical plate to the spinal vertebras. The through-openings comprise a first diameter at the front surface of the elongated body, a second diameter at the back surface of the elongated body and a third diameter in the area between the front and back surfaces of the elongated body and the first diameter is smaller than the third diameter, thereby forming a lip at the top of the through-openings and the third diameter is larger than the second diameter and the first diameter is larger than the second diameter, thereby forming a groove within the perimeter of the inner wall of the through-openings. The bone fasteners comprise a threaded main body and a head and the threaded main body comprises threads for engaging the spinal vertebras and the head comprises a cylindrical main body and one or more breakable structures configured to be flexed and inserted into the groove and then break and unflex upward and remain captured within the groove. Each of the one or more breakable structures comprises a curved body that extends tangentially from a first location of an outer side of the cylindrical main body and curves around a portion of the cylindrical main body and terminates and attaches to a second location of the outer side of the cylindrical main body.

Implementations of this aspect of the invention may include one or more of the following features. The diameter of the bone fastener head including the breakable structures in an unflexed position is larger than the first diameter of the through openings and the breakable structures are configured to flex inward toward the outer side surface of the cylindrical main body when they come in contact with the lip while the bone fastener is rotated clock-wise to be driven into the vertebras and then the breakable structures are configured to break and detach from at the second location of the outer side of the main cylindrical body and unflex upward once they are below the lip. The bone fastener head comprises an opening extending into the threaded main body and the opening comprises an inner surface having six inward protruding lobes and a bottom having six grooves. The assembly further includes a driver tool, and the driver tool comprises an elongated shaft, a handle attached to the proximal end of the elongated shaft and a bone fastener-engaging component attached to the distal end of the elongated shaft and the bone fastener-engaging component comprises one or more structures that complement and engage at least one of the grooves and lobes of the bone fastener head opening, respectively. The structures of the fastener-engaging component comprise four lobes that complement and engage four of the six lobes of the bone fastener head opening and two opposite tubular protrusions configured to be positioned and engage two opposite located grooves of the bone fastener head opening. The fastener-engaging component comprises a driver and a locking sleeve and the driver comprises an elongated cylindrical body having the structures at its distal end and a slot extending along the driver tool axis and the cylindrical body flexes and snaps into the bone fastener opening and the locking sleeve is configured to move down and lock the driver into the bone fastener head opening. The locking sleeve comprises a tubular cylindrical body and a central blade and the tubular cylindrical body is dimensioned to fit and slide over the driver cylindrical elongated body and wherein the central blade is configured to be placed within the driver slot. The breakable structures comprise curved, angled or beveled outer surfaces and the breakable structures outer surfaces cooperate with matching outer surfaces of the lip. The bone fastener head comprises an opening extending into the threaded main body and the opening comprises pentagonal, hexagonal or octagonal geometric shape. The bone fastener head comprises an opening extending into the threaded main body and the opening comprises inner threads. The elongated body comprises a first straight side surface, a second contoured side surface opposite to the first side surface, the front and back surfaces and top and bottom surfaces and the elongated body further comprises one or more elongated openings configured to support bone graft material. The through-openings comprise an oval-shaped perimeter at the back surface and the oval-shaped perimeter comprises two parallel straight sides and two opposite curved sides and the distance between the two parallel straight sides is smaller than the major diameter of the threads of the bone fasteners and wherein the distance between the curved sides is equal to or larger than the major diameter of the threads of the bone fasteners. The bone fasteners further comprise a tapered portion extending between the threaded main body and the head and the parallel straight sides of the through-openings cut into the diameter of the tapered portion for a tighter secure lock and fit. The through-openings further comprise laser-etched ridges extending perpendicular to the groove. The back surface of the cervical plate comprises a roughened texture.

In general in another aspect the invention features a bone fastener including a threaded main body and a head. The threaded main body includes threads and the head includes a cylindrical main body and one or more breakable structures configured to be flexed and inserted into a groove and then break and unflex upward and remain captured within the groove. Each of the one or more breakable structures comprises a curved body that extends tangentially from a first location of an outer side of the cylindrical main body and curves around a portion of the cylindrical main body and terminates and attaches to a second location of the outer side of the cylindrical main body.

In general in another aspect the invention features a method for stabilizing two adjacent spinal vertebras, including the following. First, providing a cervical plate comprising an elongated body having two or more through-openings extending from the front surface to the back surface of the elongated asymmetric body. Next, inserting two or more bone fasteners through the two or more through-openings, respectively, and attaching them to two or more locations in the two adjacent spinal vertebras, respectively, thereby attaching the cervical plate to the spinal vertebras. The through-openings comprise a first diameter at the front surface of the elongated body, a second diameter at the back surface of the elongated body and a third diameter in the area between the front and back surfaces of the elongated body and the first diameter is smaller than the third diameter, thereby forming a lip at the top of the through-openings and the third diameter is larger than the second diameter and the first diameter is larger than the second diameter, thereby forming a groove within the perimeter of the inner wall of the through-openings. The bone fasteners comprise a threaded main body and a head and the threaded main body comprises threads for engaging the spinal vertebras and the head comprises a cylindrical main body and one or more breakable structures configured to be flexed and inserted into the groove and then break and unflex upward and remain captured within the groove. Each of the one or more breakable structures comprises a curved body that extends tangentially from a first location of an outer side of the cylindrical main body and curves around a portion of the cylindrical main body and terminates and attaches to a second location of the outer side of the cylindrical main body.

BRIEF DESCRIPTION OF THE DRAWINGS

Referring to the figures, wherein like numerals represent like parts throughout the several views.

DETAILED DESCRIPTION OF THE INVENTION

The present invention relates to a system and method for a cervical plate assembly that includes an asymmetric bone plate and screws attaching the plate to vertebral elements.

The screws include a self-contained locking mechanism that prevents accidental disengagement of the screws due to stresses after they have been attached to the vertebral elements.

Figure 1:
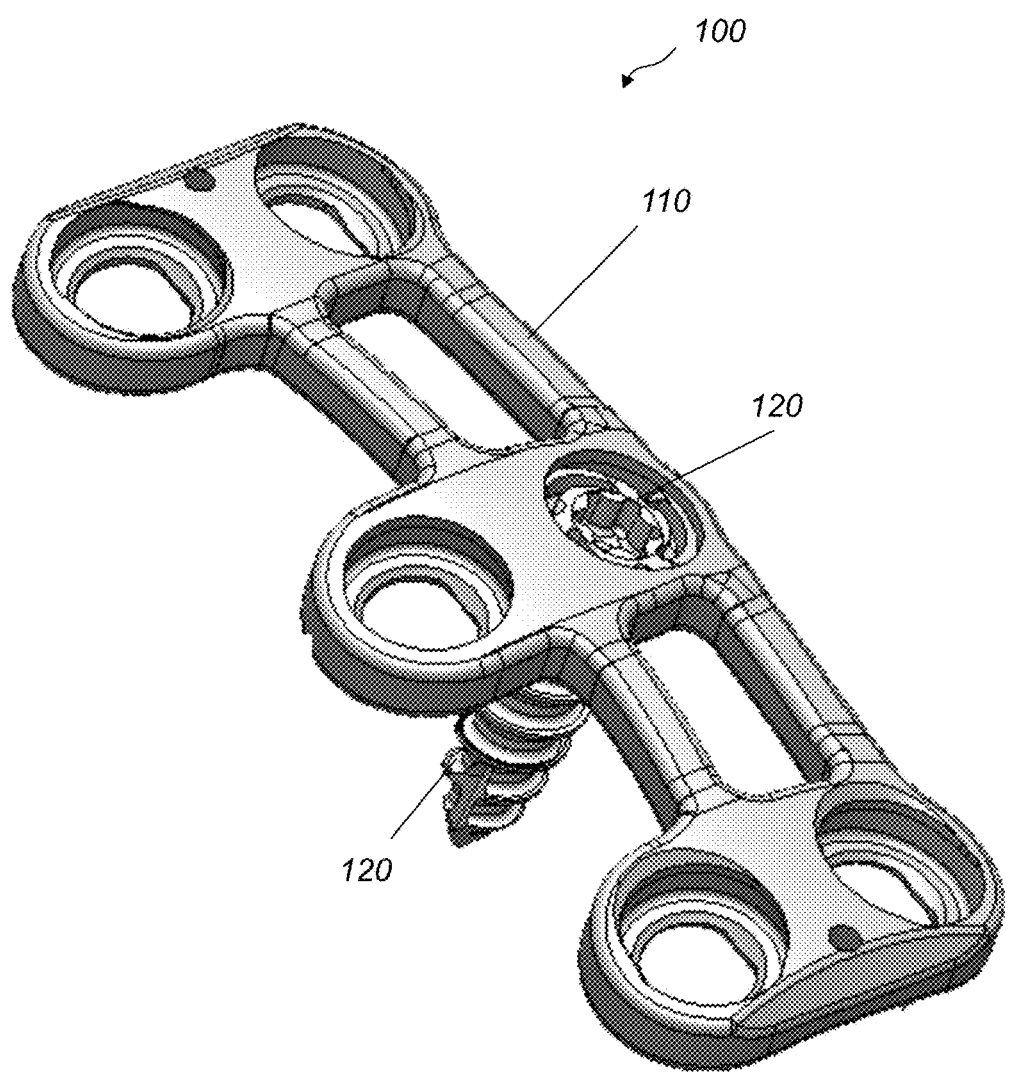
FIG. 1 is a perspective view of a cervical plate assembly, according to this invention.
Figure 2A:
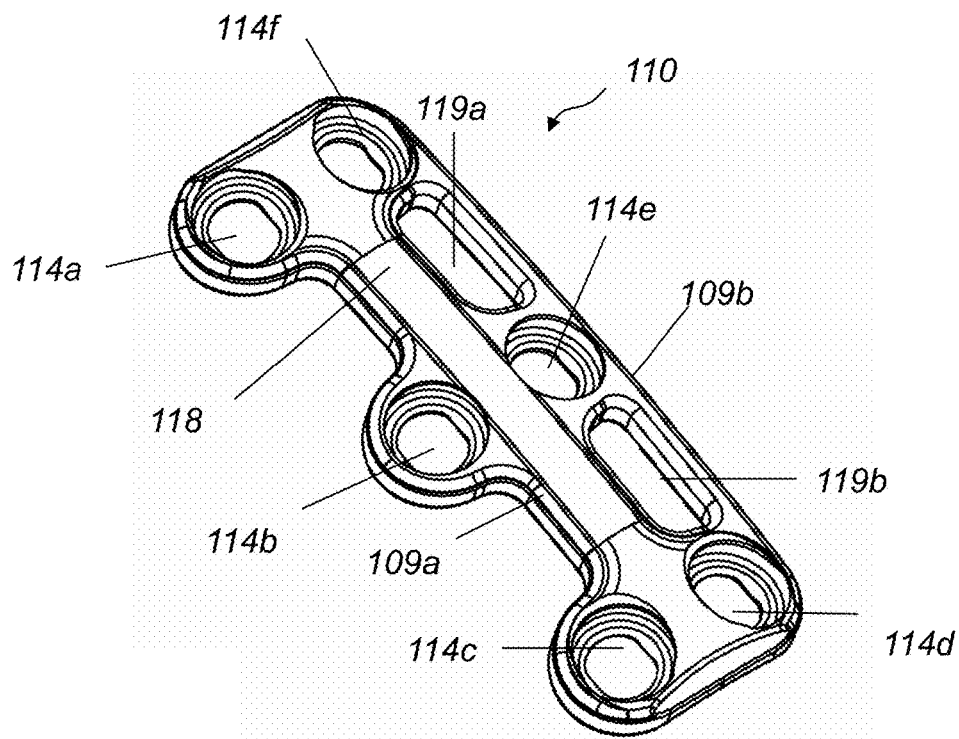
FIG. 2A is a perspective view of the cervical plate of FIG. 1.
Figure 2B:
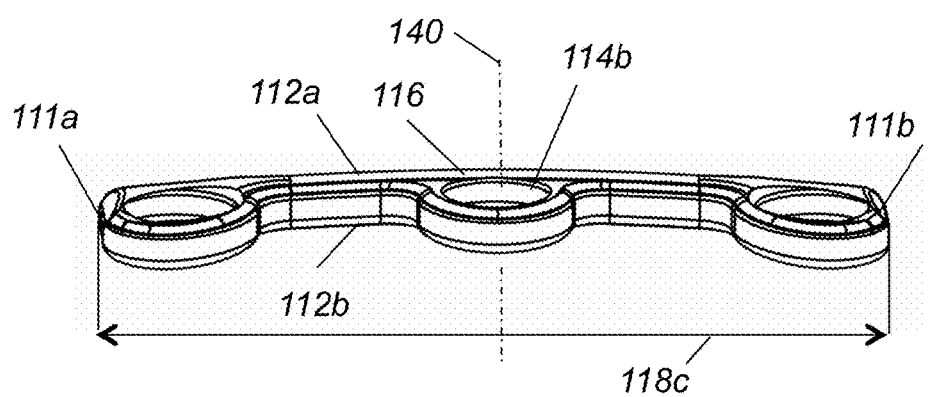
FIG. 2B is a side view of the cervical plate of FIG. 2A.
Figure 3:
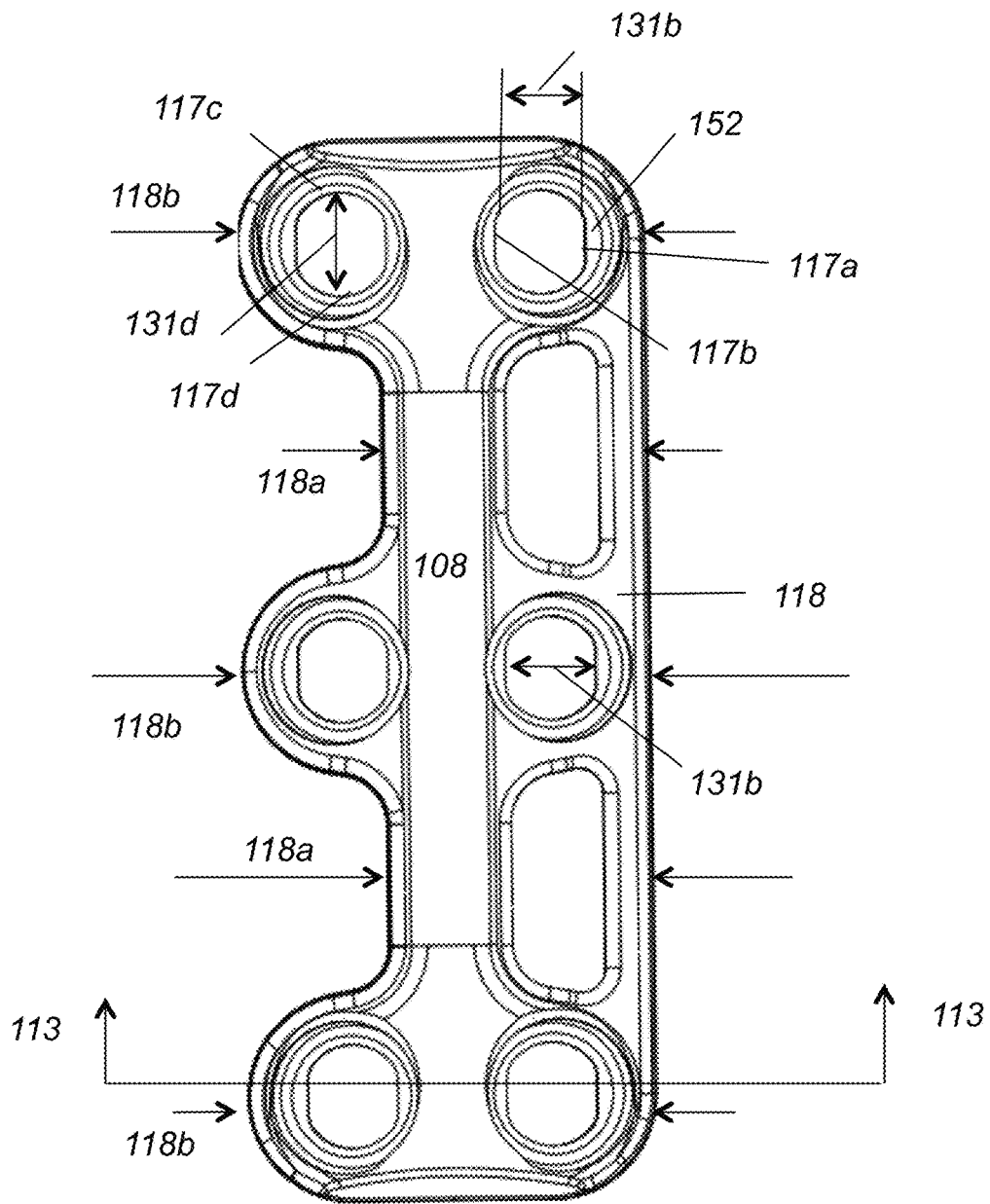
FIG. 3 is a top view of the cervical plate of FIG. 2A.
Figure 4A:
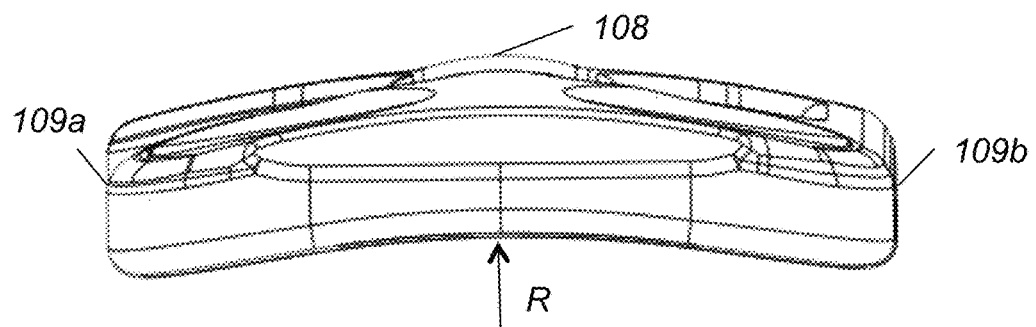
FIG. 4A is a side view of end 111b of the cervical plate of FIG. 2B.
Figure 4B:
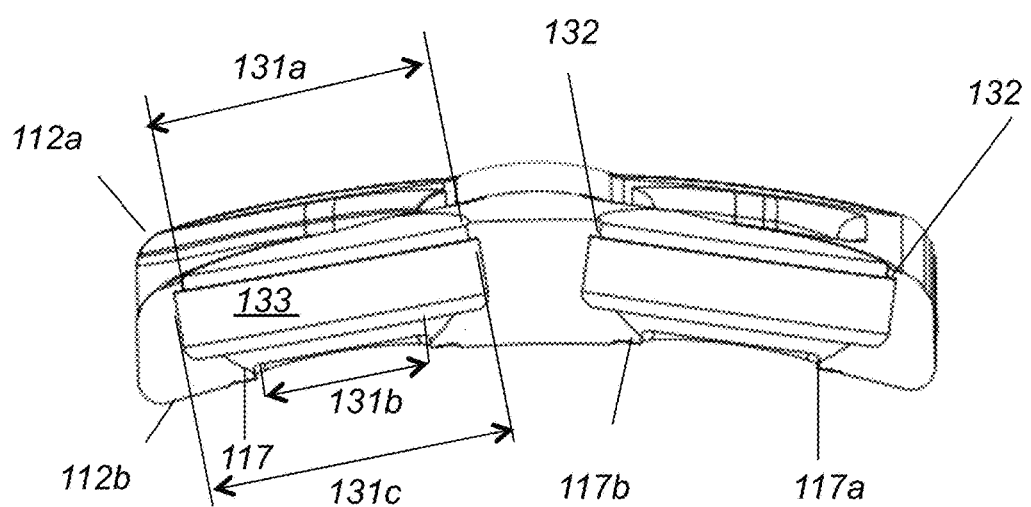
FIG. 4B is a cross-sectional view of the cervical plate along line 113.
Figure 5A:
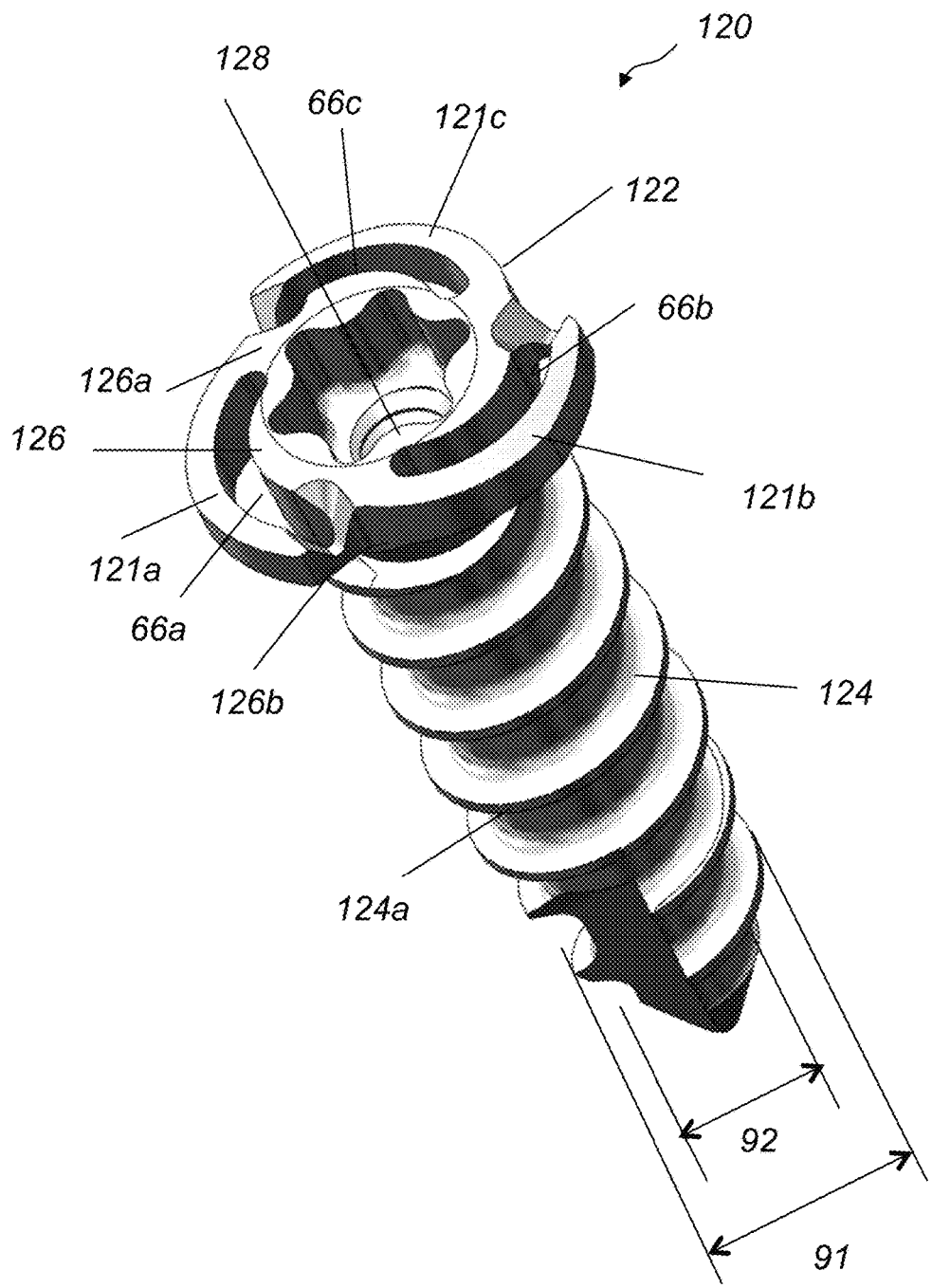
FIG. 5A is a perspective view of the screw of FIG. 1 before engaging an opening of the cervical plate.
Figure 10:
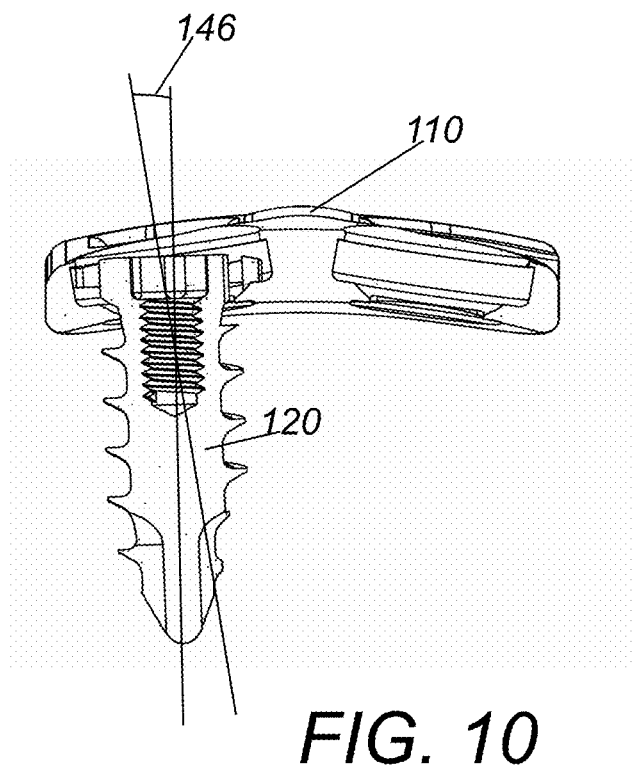
FIG. 10 is a cross-sectional view depicting an angular placement of a the screw within an opening of the cervical place.
Figure 9A:
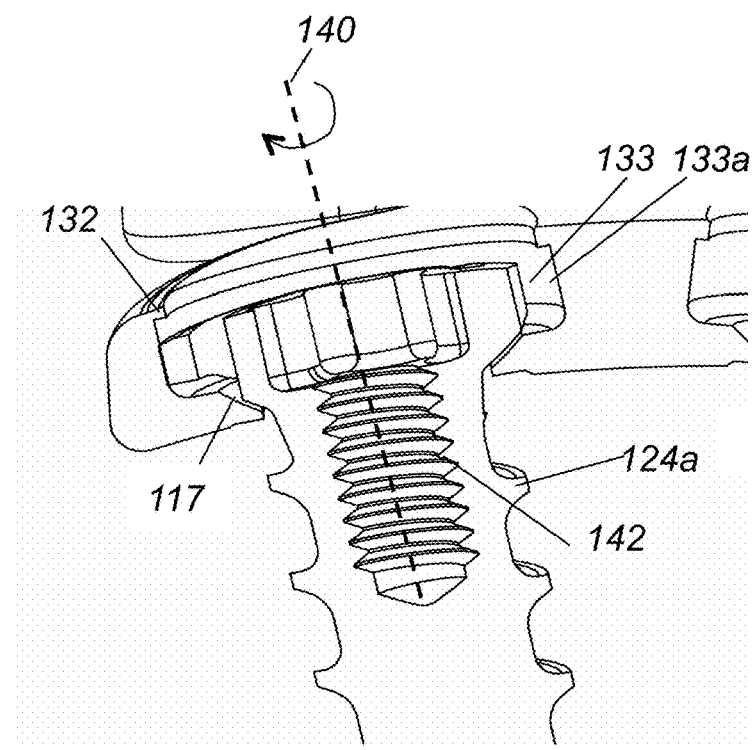
FIG. 9A is a detailed side view of area A in FIG. 8.
Figure 9B:
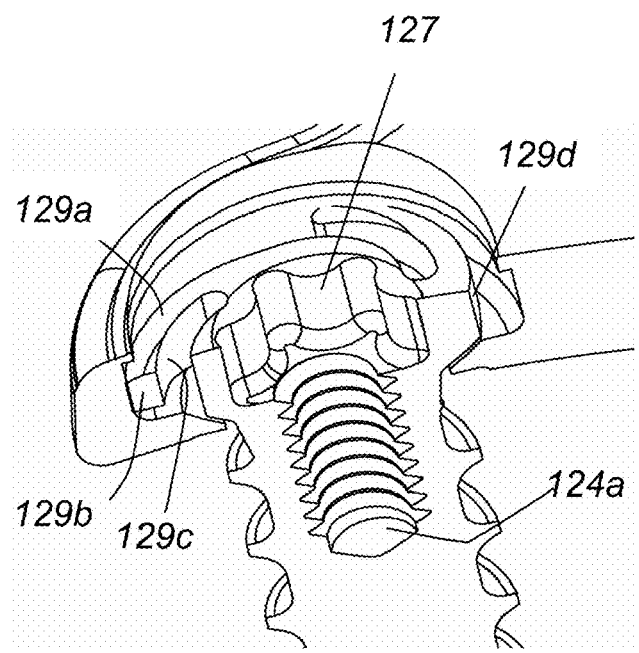
FIG. 9B is a detailed top view of area A in FIG. 8.

Referring to FIG. 1, cervical plate assembly 100 includes a cervical plate 110 and screws 120. Cervical plate 110 is a two-level bone plate configured to stabilize three adjacent vertebras (not shown). Referring to FIG. 2A, FIG. 2B, FIG. 3, FIG. 4A and FIG. 4B, plate 110 includes an elongated asymmetric body 118 that has six through-openings 114a-114f extending from the top surface 112a to the bottom surface 112b of body 118. Body 118 has one side 109b that is straight and an opposite side 109a that is contoured around the openings 114a-114c. The width 118a of plate 110 in the area inbetween openings 114a, 114b and inbetween 114b, 114c is smaller than the width 118b in the areas across openings 114a, 114f at the end 111a of the plate, across openings 114c, 114d at the end 111b of the plate and across openings 114b, 114e at the center 116 of the plate. In one example, body 118 has a length 118c of 43 millimeters, a width 118a of 13 millimeters and a width 118b of 17 millimeters. There are also two additional through-openings 119a, 119b arranged along the straight side 109b of the plate between two adjacent main openings 114f, 114e and 114e, 114d, respectively. The reduced width 118a of the plate due to the contoured side 109a and the presence of openings 119a, 119b along the straight side 109b help improve the line of sight. Openings 119a, 119b are also used for inserting bone graft material. Cervical plate 110 is also curved along its width and is thicker along the center 108 relative to the sides 109a, 109b. In one example, the plate thickness at the center is 2.55 millimeters, the width at the sides is 2.3 millimeters and the curvature R along its width 27 millimeters. The increased thickness along the center 108 provides stability and additional strength. The overall plate thickness is kept at a minimum level in order to maintain a low profile and the overall contour of the plate is configured to provide improved anatomical interface. Cervical plate ends 111a, 111b are chamfered to minimize damage of the adjacent soft tissue. Through-openings 114a-114f receive the screws 120, which are used to attach the plate 110 to the vertebras. Openings 114a-114f have an essentially circular perimeter at the top surface 112a of the plate. The diameter 131a of each opening 114a-114f near the top surface 112a is larger than the diameter 131b near the bottom surface 112b, as shown in FIG. 4B. Both top and bottom diameters 131a, 131b are smaller than the diameter 131c at the center of the opening. In one example, diameter 131a is 6 millimeters, diameter 131b is 4.20 millimeters and diameter 131c is 6.4 millimeters. A lip 132 is formed around each opening 114a-114f near the top surface 112a. Lip 132 is designed to interface with breakable components 121a-121c of the screw head 122 and thereby to lock the screw 120 onto the plate 110, as will be explained below. Openings 114a-114f have a chamfered bottom portion 117, as shown in FIG. 4B. Chamfered bottom portion 117 allows the screws 120 to assume variable trajectory and angled orientation when engaged in the vertebral bone, as shown in FIG. 10. In some embodiments, polyaxial screws 120 are used and the chamfered bottom 117 allows them to be positioned at a desired angular orientation 146 prior to being locked. The bottom portion 117 of the openings 114a-114f is oval-shaped and has two parallel straight sides 117a, 117b and two opposite curved sides 117c, 117d. The distance between the two parallel straight sides 117a, 117b (width of the opening) 131b is smaller than the major diameter 91 of the threaded portion 124 of the screw 120 and equal or larger than the minor diameter 92 of the threaded portion 124, shown in FIG. 5A. The distance 131d between the curved sides 117c and 117d of the opening (diameter) is larger or equal to the major diameter 91 of the threaded portion 124 of the screw. The oval-shaped structure of the bottom portion 117 of openings 114a-114f cooperates with the screw threads 124a to allow the screw 120 to move downward or upwards through the opening when the screw 120 is rotated and prevents backing out or moving forward of the screw 120 when the screw is pushed up or down, respectively. Since the width 131b of the opening at the bottom portion 117 is smaller than the major diameter 91 of the threaded portion 124 of the screw 120 and the diameter 131d is larger or about the same size as the major diameter 91 of the threaded portion 124, the screw threads 124a move through the opening as they are rotated clock-wise only when they are in line with the diameter 131d. Once the screw threads 124a pass below the bottom portion 117 of the opening, they cannot be accidentally pushed straight up because they will hit the straight parallel sides 117a, 117b of the oval-shaped opening, whose spacing 131d is smaller than the major diameter 91 of the screw. This "threading" of the screw 120 through the oval-shaped opening (i.e. "captive geometry") of the bottom portion 117 of the plate 110 locks the screw 120 to the plate 110 and prevents accidental backing out of the screw 120. Furthermore, screw 120 includes a tapered portion (angled sides 125a, 125b) and at this tapered portion the straight parallel sides 117a, 117b cut into the diameter of the tapered portion for a tighter secure lock and fit. Plate 110 is also described in U.S. application Ser. No. 13/785,279 filed Mar. 5, 2013 and entitled "CERVICAL PLATE ASSEMBLY", which is commonly owned and the contents of which are expressly incorporated herein by reference.

Figure 7A:
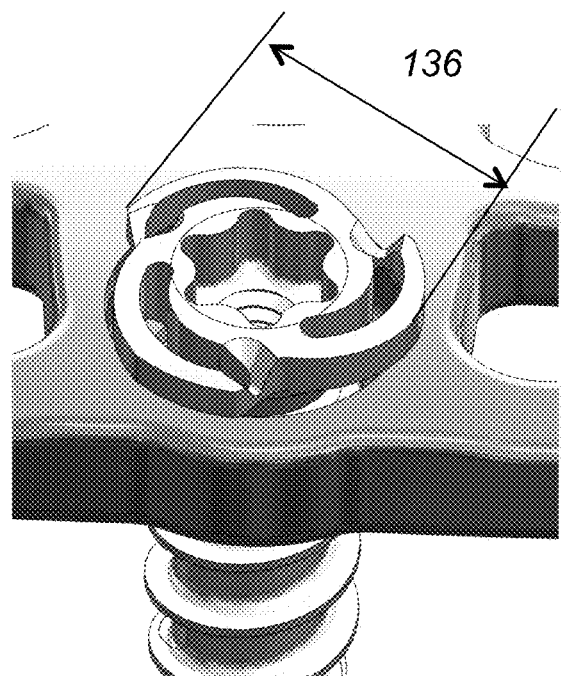
FIG. 7A is a top perspective view of the screw of FIG. 5A before engaging an opening of the cervical plate.
Figure 7B:
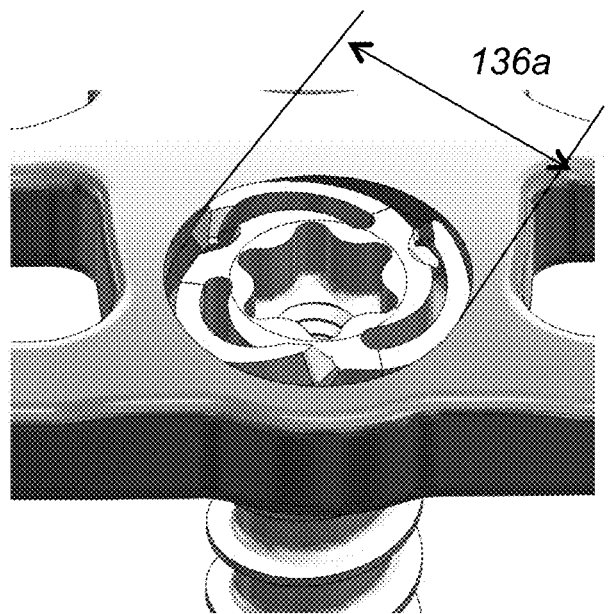
FIG. 7B is a top perspective view of the screw of FIG. 7A as it starts to engage an opening of the cervical plate.
Figure 7C:
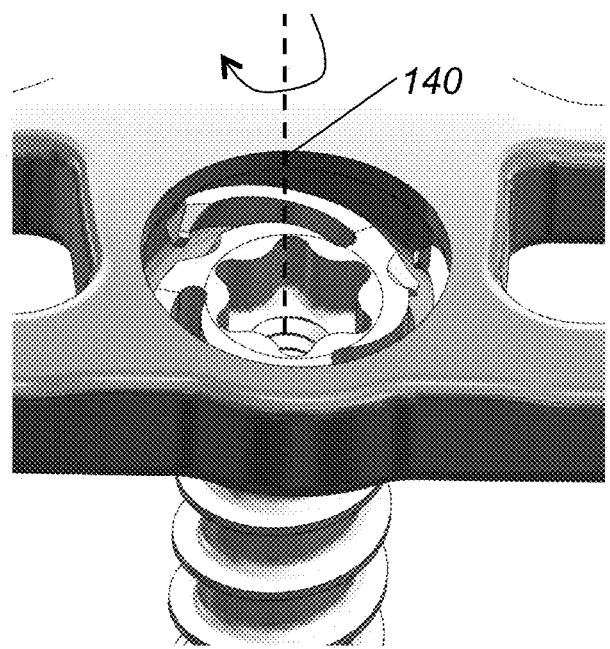
FIG. 7C is a top perspective view of the screw of FIG. 7A after it has fully engaged an opening of the cervical plate.
Figure 7D:
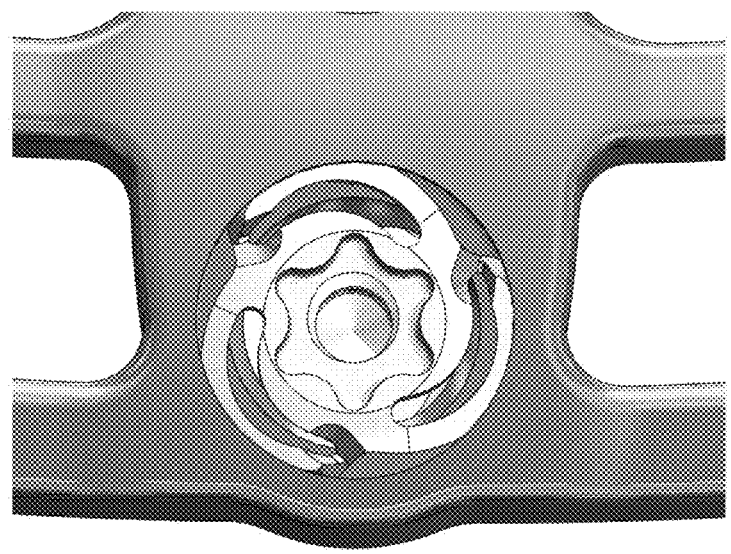
FIG. 7D is a top view of the screw of FIG. 7C.
Figure 8:
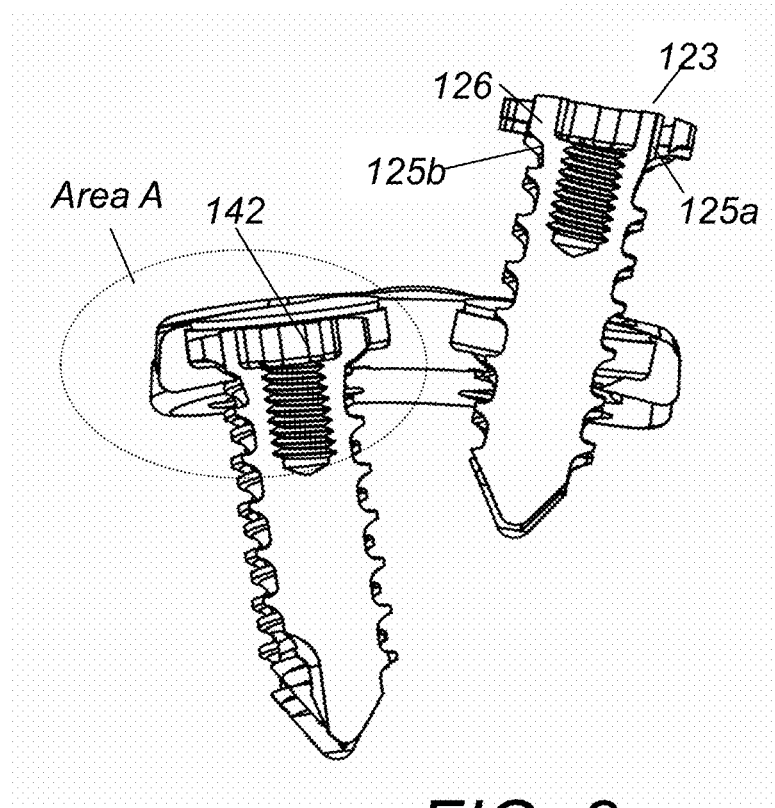
FIG. 8 is a cross-sectional view of the cervical plate assembly.

Referring to FIG. 5A to FIG. 10, bone screw 120 has a threaded main body 124 and a head 122. Main body 124 includes threads 124a for engaging the vertebral bone. Head 122 has a flat top 123, a cylindrical center 126, three breakable components 121a, 121b, 121c, and a tapered portion 125 with angled bottom sides 125a, 125b, as shown in FIG. 8. Top 123 includes an opening 128 extending into the main body 124. Opening 128 has six lobes 127a-127f, and at the bottom between two adjacent lobes six grooves 99a-99f are formed, as shown in FIG. 11F. As will be explained later, the geometry of opening 128 interfaces with the geometry of a screw engaging component 284 to lock a driver tool 200 into the opening 128, as shown in FIG. 11B.

Figure 5B:
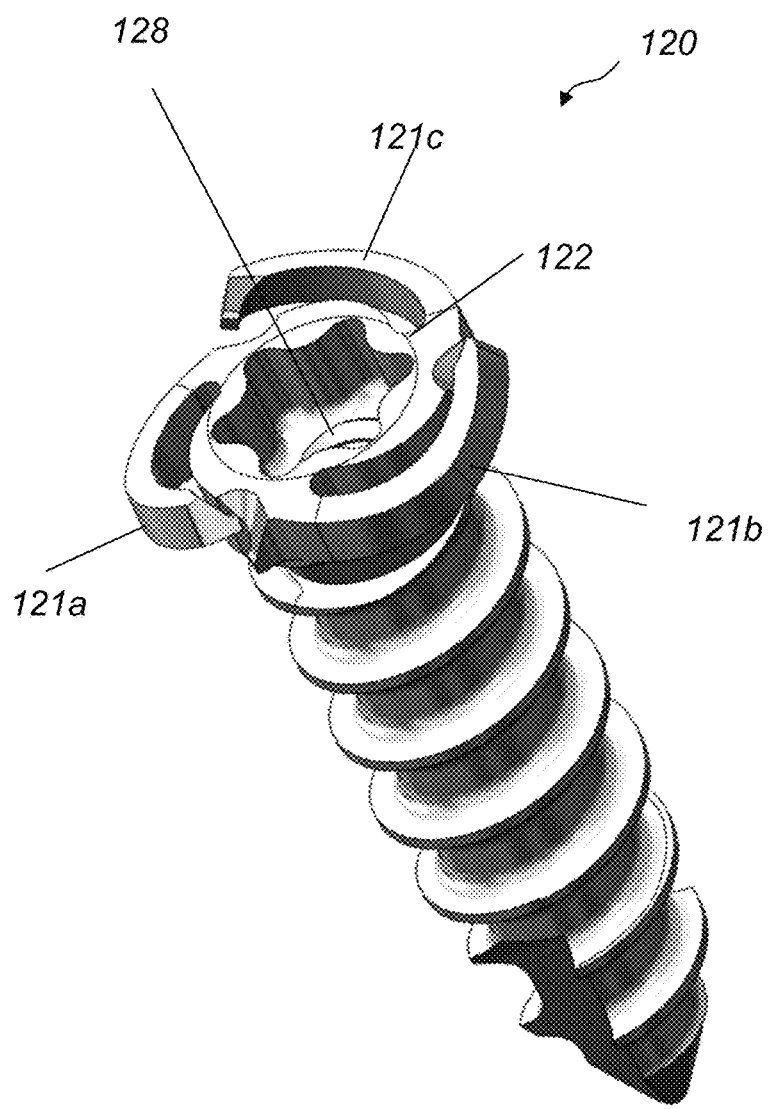
FIG. 5B is a perspective view of the screw of FIG. 1 after engaging an opening of the cervical plate.
Figure 6A:
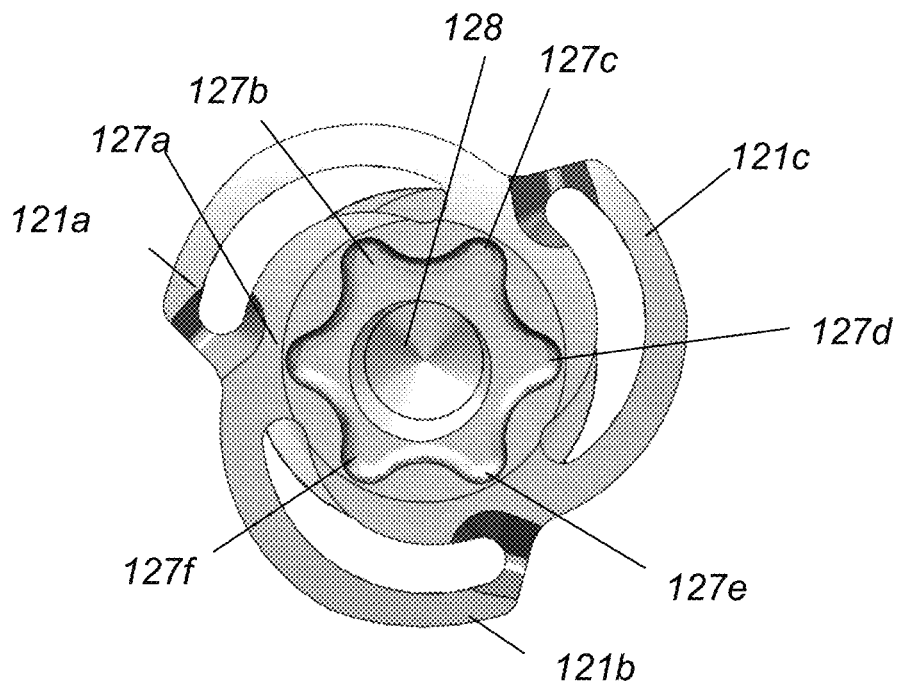
FIG. 6A is a top view of the screw of FIG. 5A.
Figure 6B:
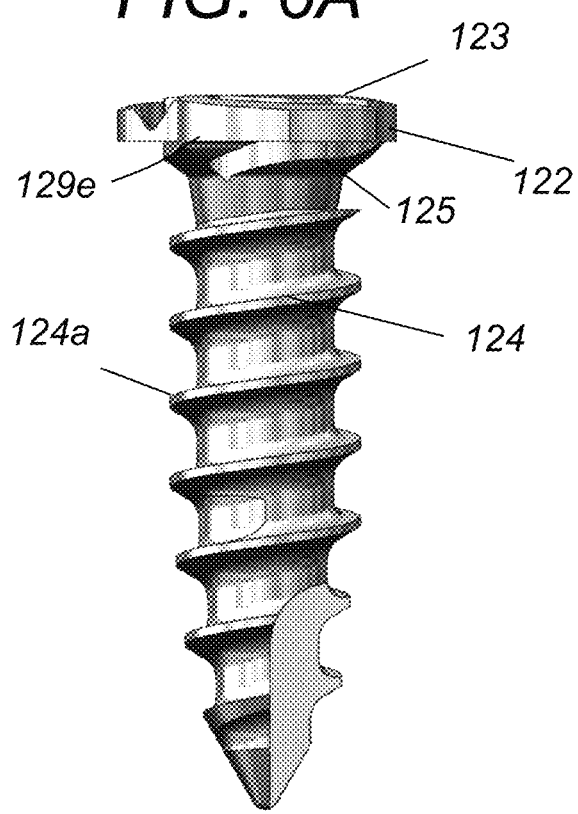
FIG. 6B is a side view of the screw of FIG. 5A.

Each of the breakable components 121a-121c includes a curved body that extends tangentially from a first location of the outer side of the cylindrical center 126, curves around the center 126 and terminates at a second location of the outer side of the cylindrical center 126. Breakable components 121a-121b are initially attached to the cylindrical center 126 at both the first and second locations, and gaps 66a-66c are formed between the outer surface of the cylindrical center 126 and the breakable component 121a-126c. In one example, breakable component 121a extends from location 126a of the outer surface of the cylindrical center 126 and terminates at location 126b of the outer side of the cylindrical center 126. Breakable component 121a is initially attached to both locations 126a and 126b and a gap 66a is formed between the outer surface of the cylindrical center 126 and the breakable component 121a. The connection between the breakable component 121a and the outer surface of the cylindrical center 126 at point 121b is weak and breaks when the screw head 122 engages the opening 114a of the cervical plate 110, as shown in FIG. 5B. FIG. 7A depicts the head 122 of screw 120 just before it engages opening 114a of the cervical plate 110. FIG. 7B depicts the head 122 of screw 120 immediately after it engaged opening 114a of the cervical plate 110. As shown, one end of each of the breakable components 121a-121c breaks and detaches from the cylindrical center 126. As the screw 120 continues to engage the bone, the detached ends of the breakable components 121a-121c flex upward, as shown in FIG. 7C.

The effective diameter 136 of the screw head 122 including the breakable components 121a-121c in the initial position of FIG. 7A is larger than the top diameter 131a of openings 114a-114f. Breakable components 121a-121c flex inward toward the central axis 140 when they come in contact with lip 132 of the openings 114a-114f while the screw 120 is being rotated clock-wise to be driven into the vertebral body. This inward flexing causes the breakable components 121a-121c to break away from the cylindrical body 126 at their corresponding second locations. The effective diameter 136a of the screw head 122 including the breakable components 121a-121c in the inward flexed position is smaller than the top diameter 131a of openings 114a-114f, and this allows the screw head 122 including the breakable components 121a-121c to move below the lip 132, as shown in FIG. 7B. Once the breakable components 121a-121c are below the lip 132 they expand back up to their unflexed position within the space 133 formed in the opening 114a between the lip 132 and the chamfered sides at the bottom portion 117 of the opening, as shown in FIG. 7C. Once the entire screw head 122 is in place within space 133, the lip 132 prevents the screw head from accidentally moving up (i.e., backing out) from space 133 due to stresses applied during spinal motion. In cases where the mounted screw is rotated counter-clockwise, breakable components 121a-121c hit the lip 132 and sidewall 133a and flex outward away from the central axis 140, thereby increasing the effective diameter of the screw head so that it is even larger than the top diameter 131a. This outward flexing of the breakable components 121a-121c prevents the screw head 122 from accidentally moving up and out of space 133. The surgeon may pull out the screw with a driver tool, as will be described below.

In operation, plate 110 is attached to the vertebras with the screws 120. During the driving in of the screws into the selected vertebral locations, the screw threads 124a cooperate with the "captive geometry" at the bottom portion of the plate 117. The breakable components 121a-121c are flexed inward and break away from the cylindrical center 126 at their corresponding second locations and then move in space 133 where they expand back up to their unflexed state. The combination of these two mechanisms, i.e., "threading" the screw 120 though the bottom portion 117 of the plate 110 and the breaking, positioning and locking of the breakable components 121a-121c in space 133, lock the screw 120 onto the plate 110 and prevent accidental disengagement due to stresses generated during motion.

Figure 11:
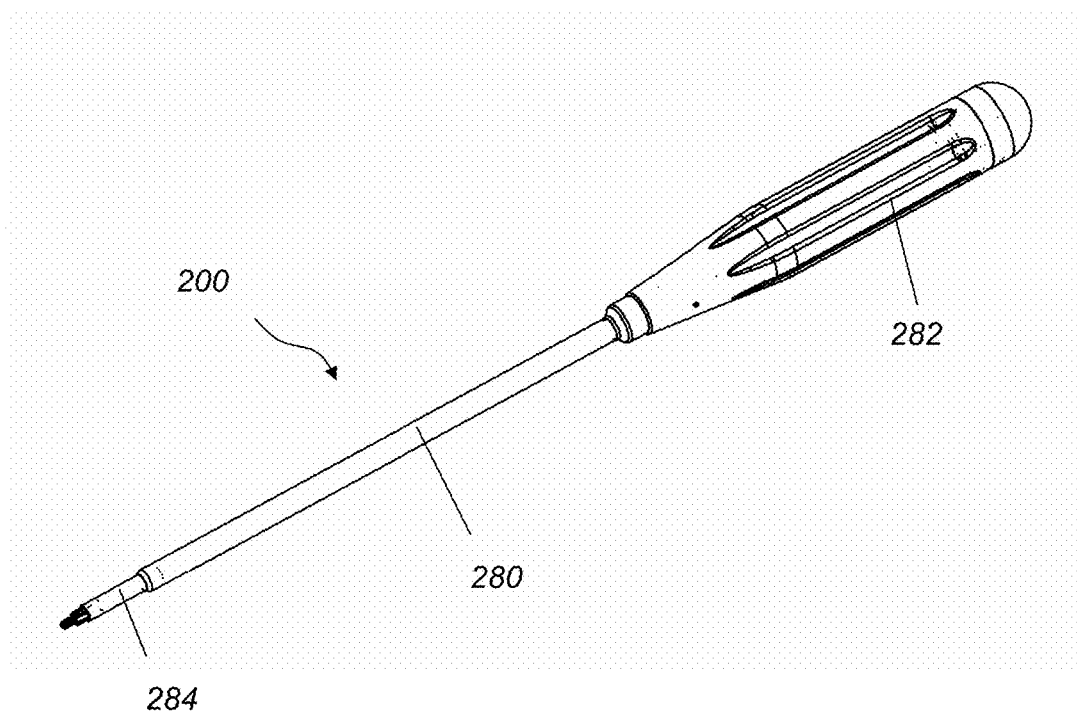
FIG. 11 depicts a two-component driver tool.
Figure 11A:
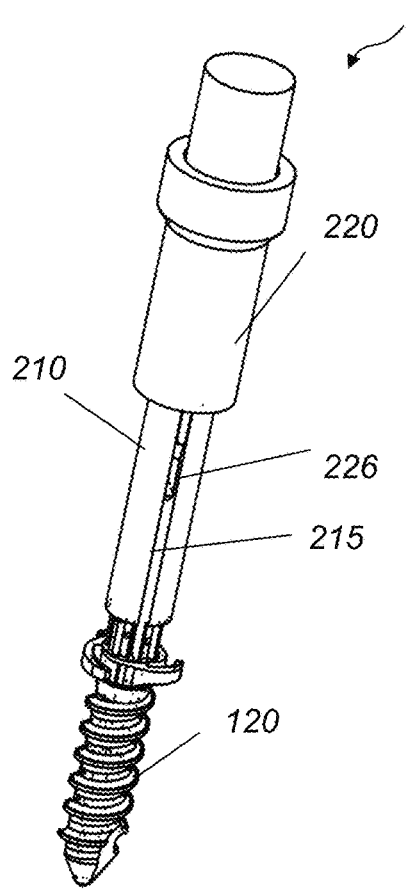
FIG. 11A depicts a driver tool end in the unlocked position.
Figure 11B:
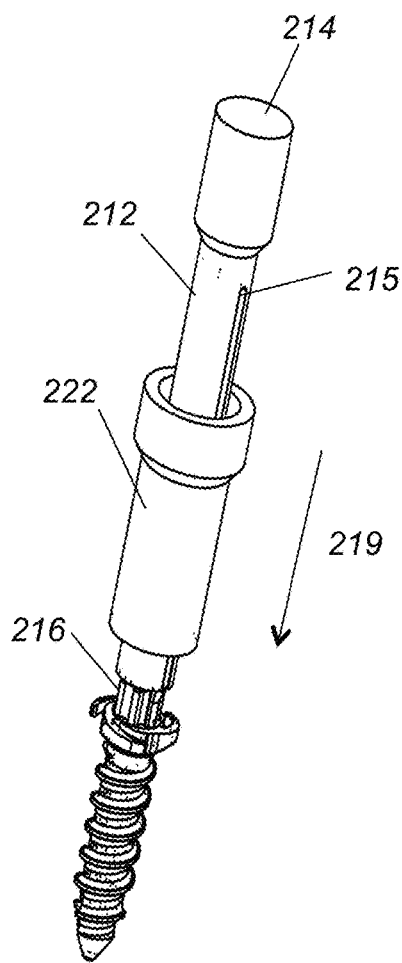
FIG. 11B depicts the driver tool end of FIG. 11A in the locked position.
Figure 11C:
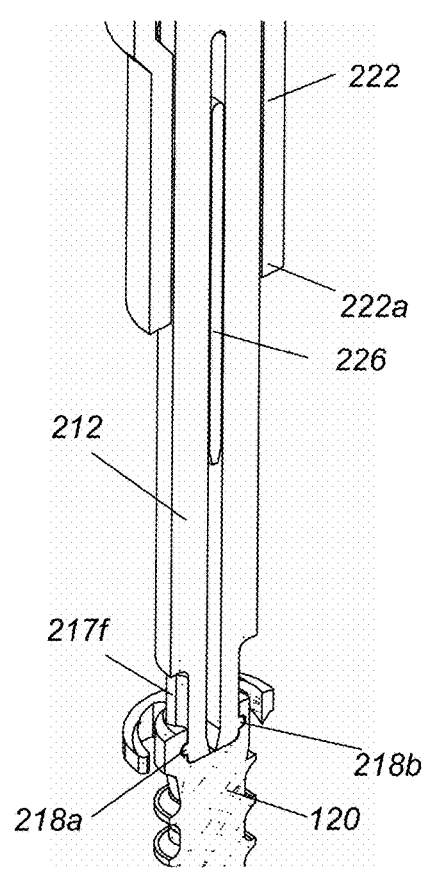
FIG. 11C is a cross-sectional view of FIG. 11A.
Figure 11D:
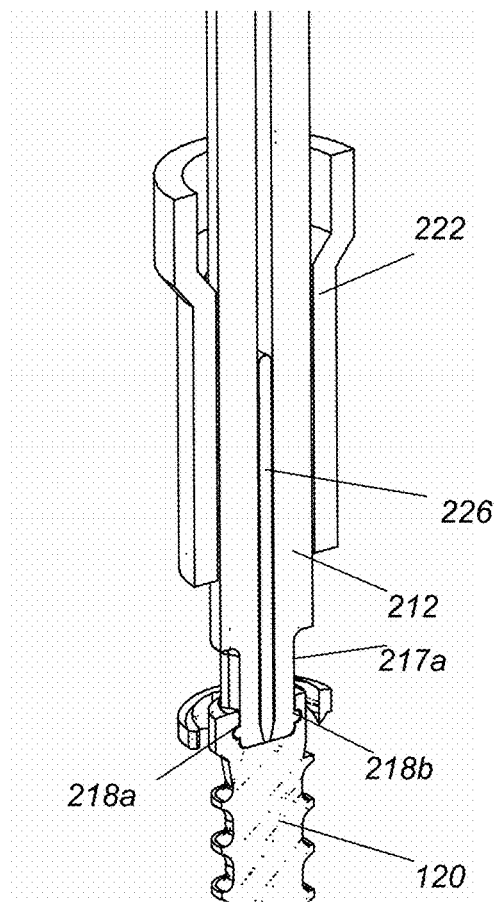
FIG. 11D is a cross-sectional view of FIG. 11B.
Figure 11E:
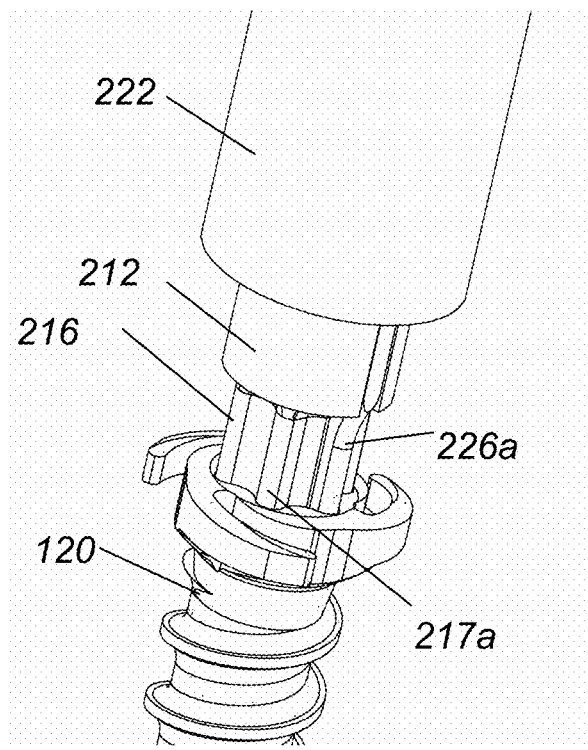
FIG. 11E is a detailed view of the lower end of the driver tool in the locked position.
Figure 12:
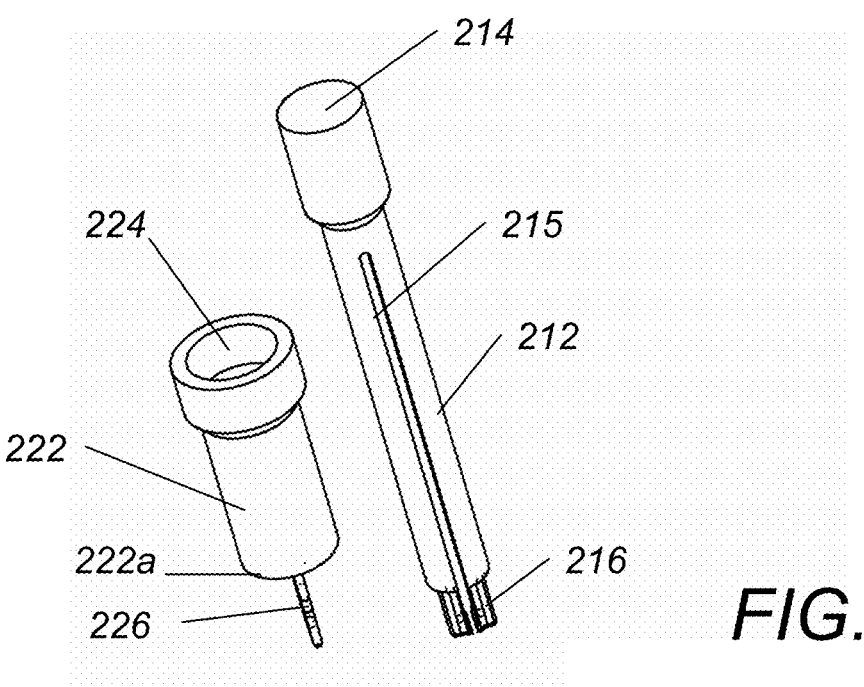
FIG. 12 is a perspective view of the driver 210 and the locking sleeve 220.
Figure 11F:
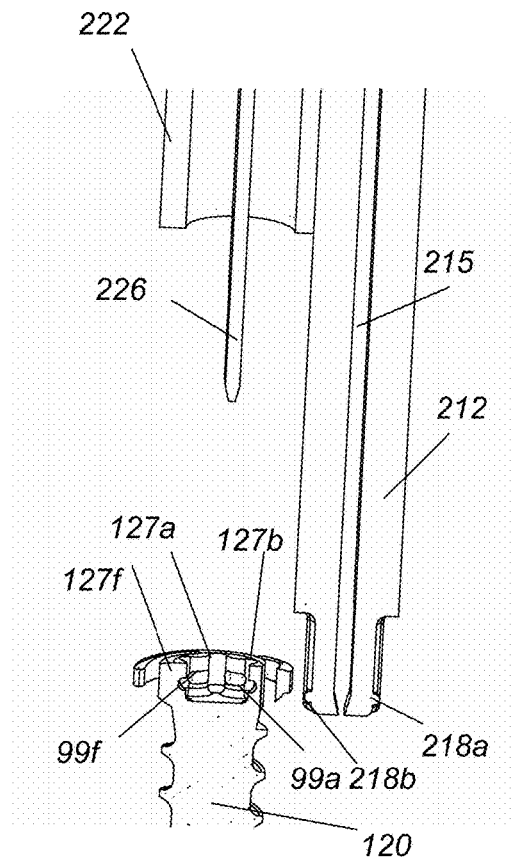
FIG. 11F is an exploded view of FIG. 11C.
Figure 13:
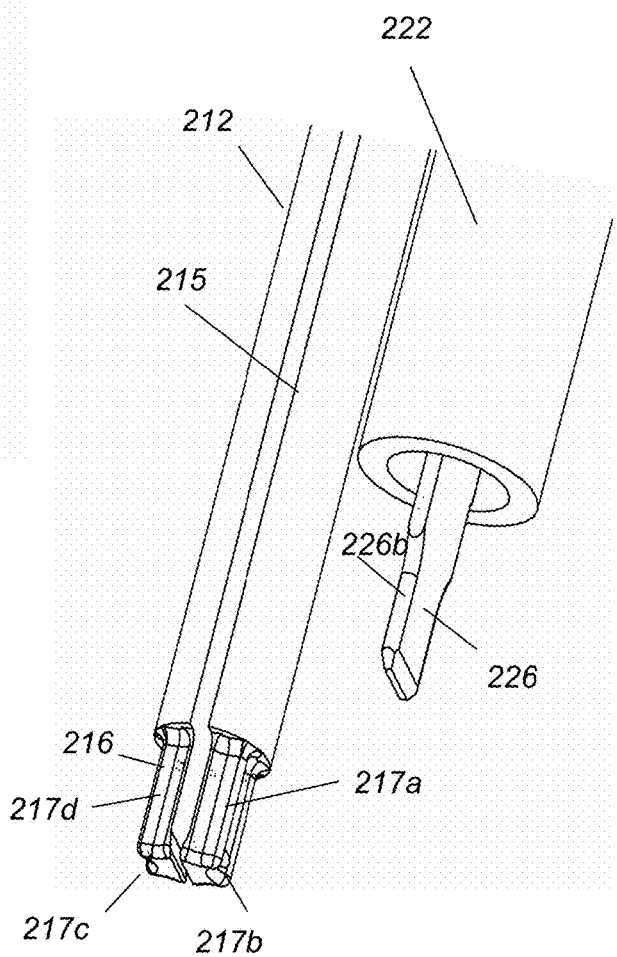
FIG. 13 is perspective view of the bottom portion of the driver 210, the locking sleeve 220 with the lowered blade 226.
Figure 11G:
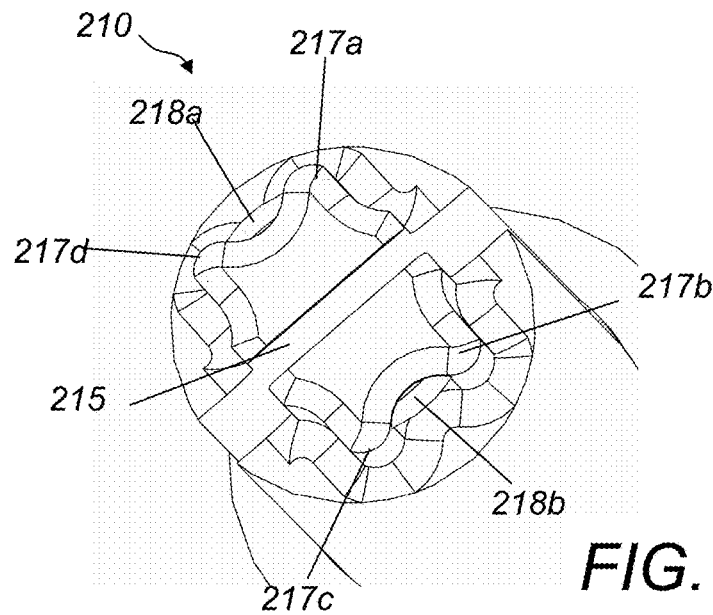
FIG. 11G is a detailed bottom view of the driver 210.
Figure 11H:
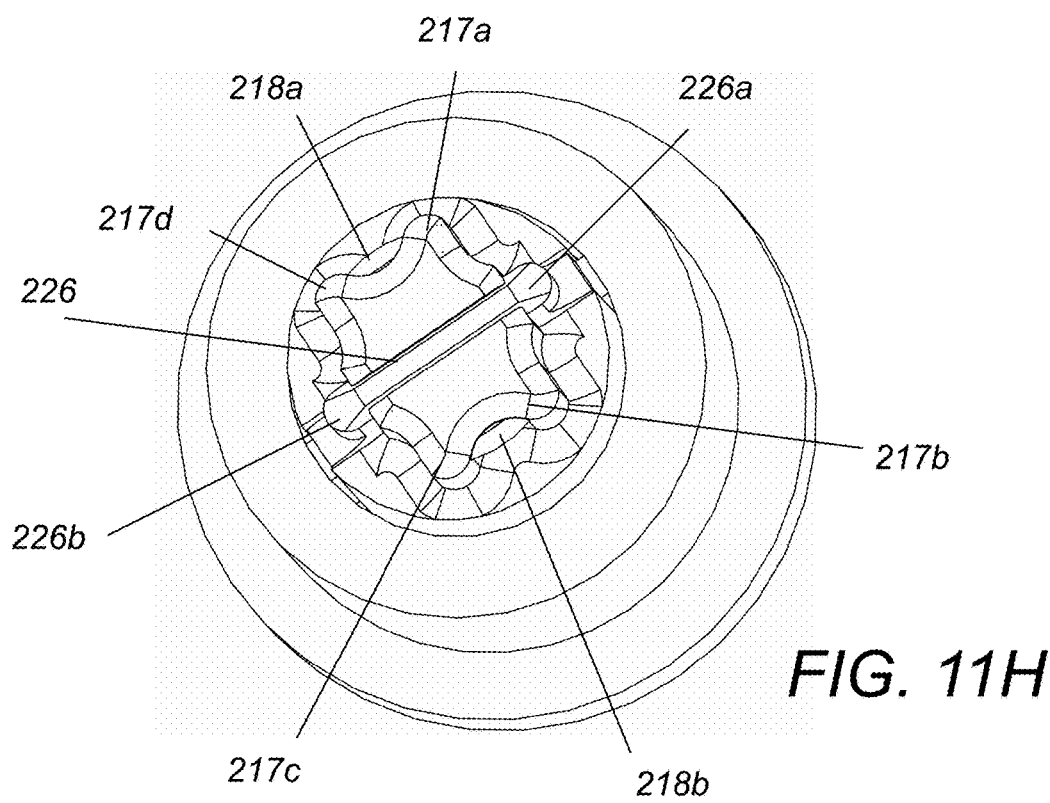
FIG. 11H is a detailed bottom view of the driver 210 with the lowered blade 226.

Referring to FIG. 11 to FIG. 13, a two-component tool 200 is used to drive screw 120 through the openings 114a-114f of the cervical plate 100 into the bone. Tool 200 includes an elongate shaft 280 having a handle 282 at its proximal end and a screw engaging component 284 at its distal end. Screw engaging component 284 includes a driver 210 and a locking sleeve 220. Driver 210 has an elongated cylindrical body 212 with a cylindrical top 214 and a driver end 216. The driver end 216 includes four lobes 217a-217d that match and interface with four of the six lobes 127a, 127c, 127d, 127f of opening 128 in the screw top 123, respectively. Driver end 216 also includes two tubular protrusions 218a, 218b positioned between lobes 217a, 217d and 217d, 217c, respectively. Protrusions 218a, 218b fit within opposite located grooves 99a and 99d formed between adjacent lobes in opening 128. The interfacing of the driver end geometry with the screw head opening 128 geometry engages the driver 210 to the screw head 122. In this engaged position, the driver is used to rotate screw 120 clockwise or counter-clockwise. An elongated slot 215 extends along the length of the cylindrical body 212 through its center and allows the body 212 to flex and snap into opening 128 of the screw head. Once the driver end 216 is snapped into opening 128, the locking sleeve 220 is moved down to lock the driver 210 into the opening 128 of the screw head. Locking sleeve 220 has a cylindrical body 222 with a diameter larger than the diameter of the cylindrical body 212 of the driver. Cylindrical body 222 has a central opening 224 extending the entire length of body 222 and a central blade 226 extending from about the middle of body 222 toward and past the lower end 222a of body 222. Driver 210 is inserted into the central opening 224 of the locking sleeve 220 and slot 215 is aligned with and placed over blade 226, as shown in FIG. 11A and FIG. 11C. After placing the driver end 216 into the screw opening 128, the locking sleeve 220 is moved down in the direction 219 so that the blade 226 is positioned in the slot area of the driver end 216, shown in FIG. 11B and FIG. 11D. The two parallel sides 226a, 226b of blade 226 protrude through the sides of slot 215, as shown in FIG. 11E. The protruding blade sides 226a, 226b interface with two opposite lobes 127b, 127e in opening 128, respectively. The placing of the blade 226 within the slot 215 in the screw head opening 128 prevents the lower end of body 212 from flexing and thereby locks the driver 210 within the screw head opening 128. The locked driver 210 is then used to rotate clockwise or counter-clockwise screw 120 into or out of the desired bone location, respectively, and to drive or pull the screw 120 in or out of place.

Figure 14A:
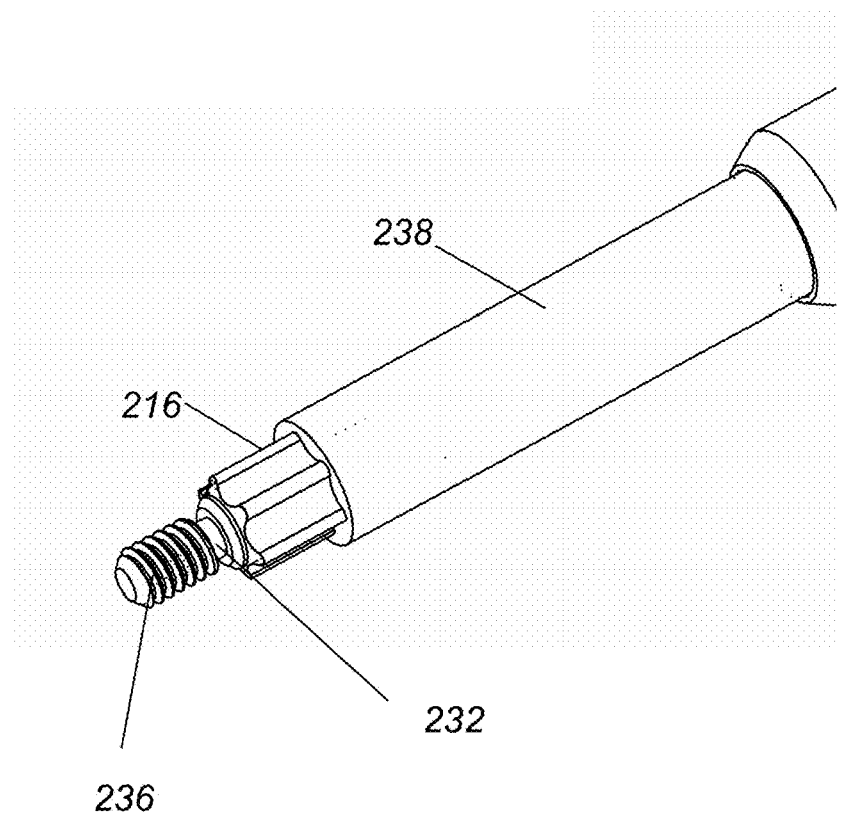
FIG. 14A depicts a driver tool end for removing a bone screw.
Figure 14B:
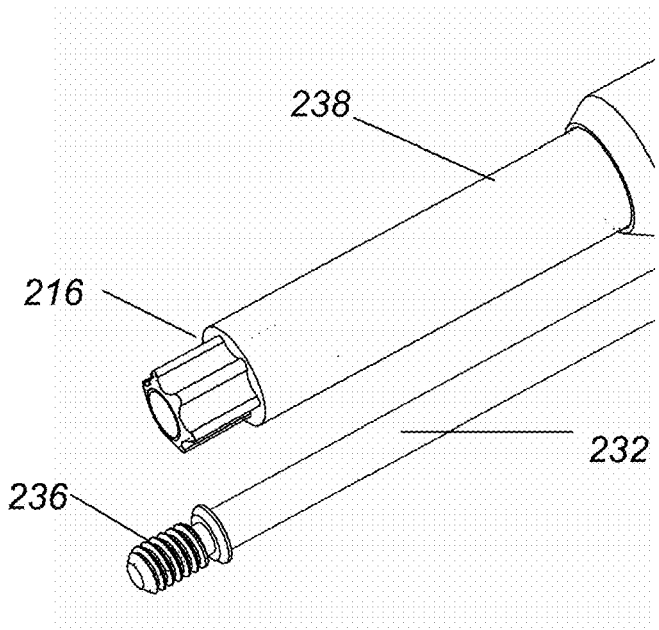
FIG. 14B is an exploded view of the driver tool end of FIG. 14A.
Figure 15A:
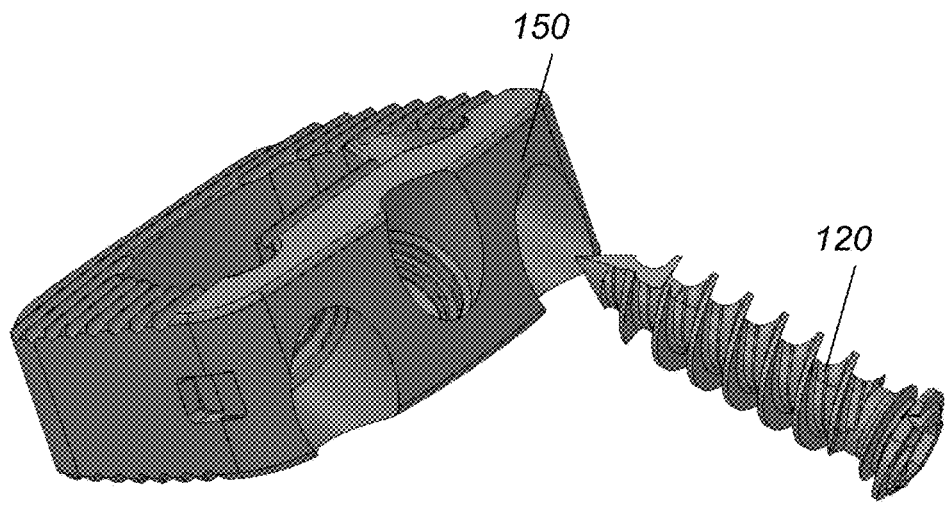
FIG. 15A and FIG. 15B are perspective views of an intervertebral component assembly, according to this invention.
Figure 15B:
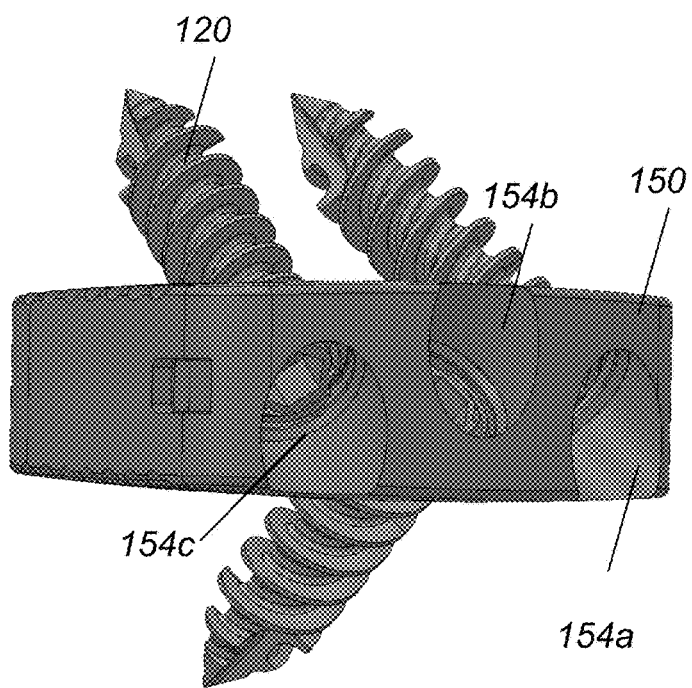
Figure 16:
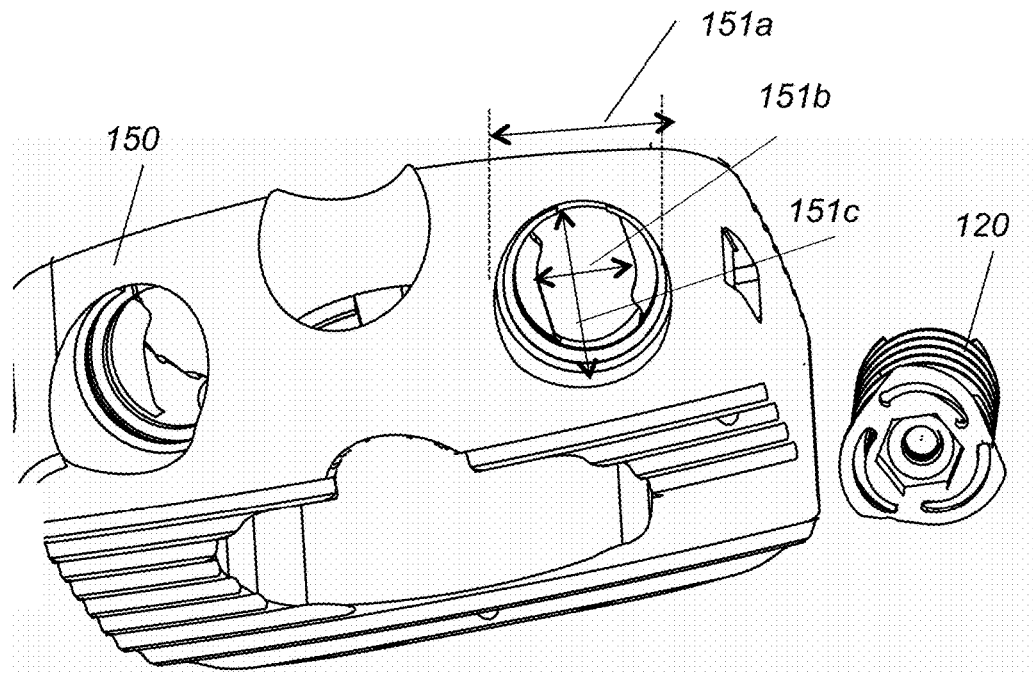
FIG. 16 is a front view of the intervertebral component 150 and screw 120 of FIG. 15A in the non-engaged position.

Referring to FIG. 14a, and FIG. 14B, the driver tool 200 includes an inner cylindrical shaft 232 having a screw 236 at its distal end, instead of an inner central blade 226. Screw 236 is used for removing a bone screw from a vertebral location. In this case, opening 128 in the bone screw head top 123 includes inner threads. Inner cylindrical shaft 232 rotates clockwise independently of the outer sleeve 238 and attaches screw 236 to the threaded hole 128, thereby locking the driver tool 200 to the screw 120. Rotating the driver tool 200 counter-clockwise removes the screw 120 from its place.

Figure 17:
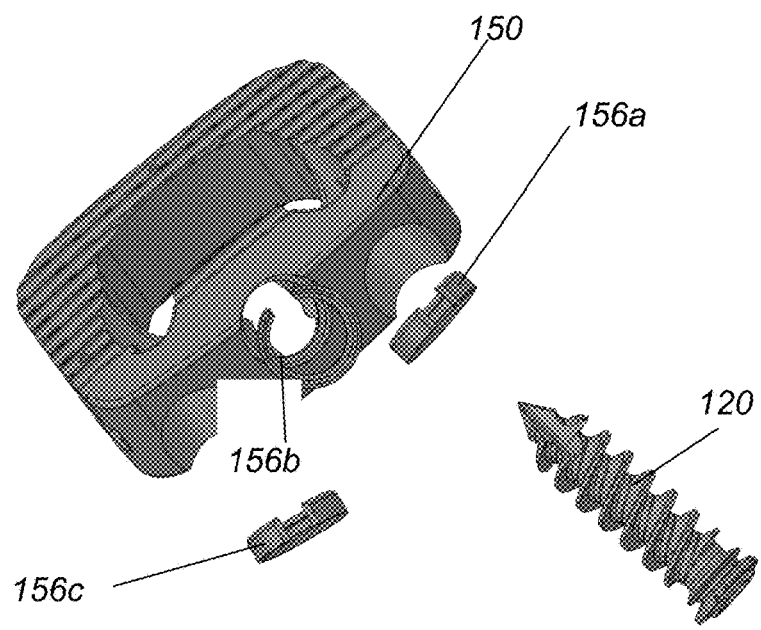
FIG. 17 is a partially exploded perspective view of the intervertebral component assembly of FIG. 15B.

Referring to FIG. 15A-FIG. 16B, screw 120 is used for securing an intervertebral component 150 to adjacent vertebras. Intervertebral component 150 includes three openings 154a, 154b, 154c that are configured to receive corresponding rings 156a, 156b, 156c and screws 120, as shown in FIG. 17 and FIG. 15B. Each openings 154a, 154b, 154c has an essentially circular perimeter at the top surface of the intervertebral component 150. The diameter 151a of each opening 154a, 154b, 154c near the top surface is larger than the diameter 151b near the bottom surface, as shown in FIG. 16A. Both top and bottom diameters 151a, 151b are smaller than the diameter 151c at the center of the opening. A lip 152 is formed around each opening 154a, 154b, 154c near the top surface. Lip 152 is designed to interface with breakable components 121a-121c of the screw head 122 and thereby to lock the screw 120 onto the intervertebral component 150, as was explained above. Intervertebral component 150 is made of polyether ether ketone (PEEK) and rings 156a-156c and screws 120 are made of metal. Metal rings 156a-156c are inserted into openings 154a-154c and prevent the metal screw head 122 from scraping and damaging the intervertebral component 150 within the openings 154a-154c. Metal breakable components 121a-121c in each screw head 122 interface with the metal rings 156a-156c in the corresponding opening 154a-154c and compress inward and break without contacting the PEEK material.

Several embodiments of the present invention have been described. Nevertheless, it will be understood that various modifications may be made without departing from the spirit and scope of the invention. Accordingly, other embodiments are within the scope of the following claims.

What is claimed is:

1. An implantable cervical plate assembly for stabilization of two adjacent spinal vertebras, comprising:
   a cervical plate comprising an elongated body having two or more through-openings extending from a front surface to a back surface of the elongated body;
   two or more bone fasteners configured to be inserted through the two or more through-openings, respectively, and attached to two or more locations in the two adjacent spinal vertebras, respectively, thereby attaching the cervical plate to the spinal vertebras;
   wherein the through-openings comprise a first diameter at the front surface of the elongated body, a second diameter at the back surface of the elongated body and a third diameter in the area between the front and back surfaces of the elongated body and wherein the first diameter is smaller than the third diameter, thereby forming a lip at the top of the through-openings and wherein the third diameter is larger than the second diameter and the first diameter is larger than the second diameter, thereby forming a single continuous groove within the perimeter of the inner wall of the through-openings;
   wherein the bone fasteners comprise a threaded main body and a head and wherein the threaded main body comprises threads for engaging the spinal vertebras and wherein the head comprises a cylindrical main body and one or more breakable structures;
   wherein each of the one or more breakable structures comprises a curved body that extends tangentially from a first location of an outer side of the cylindrical main body and curves around a portion of the cylindrical main body and terminates to a distal end that comprises a weak breakable attachment to a second location of the outer side of the cylindrical main body; and
   wherein each breakable structure is initially attached to both the first and second locations of the cylindrical main body and wherein each breakable structure is configured to be flexed and inserted into the groove and then the weak breakable attachment of the distal end is configured to break away from the second location and the broken away distal end is configured to unflex upward and to remain captured within the groove.

2. The assembly of claim 1 wherein the diameter of the bone fastener head including the breakable structures in an unflexed position is larger than the first diameter of the through openings and wherein the breakable structures are configured to flex inward toward the outer side surface of the cylindrical main body when they come in contact with the lip while the bone fastener is rotated clock-wise to be driven into the vertebras and then the breakable structures are configured to break and detach from the second location of the outer side of the main cylindrical body and unflex upward once they are below the lip.

3. The assembly of claim 1, wherein the bone fastener head comprises an opening extending into the threaded main body and wherein the opening comprises an inner surface having six inward protruding lobes and a bottom having six grooves.

4. The assembly of claim 3, further comprising a driver tool, wherein the driver tool comprises an elongated shaft, a handle attached to the proximal end of the elongated shaft and a bone fastener-engaging component attached to the distal end of the elongated shaft and wherein the bone fastener-engaging component comprises one or more structures that complement and engage at least one of the grooves and lobes of the bone fastener head opening, respectively.

5. The assembly of claim 4, wherein the structures of the fastener-engaging component comprise four lobes that complement and engage four of the six lobes of the bone fastener head opening and two opposite tubular protrusions configured to be positioned and engage two opposite located grooves of the bone fastener head opening.

6. An implantable cervical plate assembly for stabilization of two adjacent spinal vertebras, comprising:
   a cervical plate comprising an elongated body having two or more through-openings extending from a front surface to a back surface of the elongated body;
   two or more bone fasteners configured to be inserted through the two or more through-openings, respectively, and attached to two or more locations in the two adjacent spinal vertebras, respectively, thereby attaching the cervical plate to the spinal vertebras, wherein the bone fastener head comprises an opening extending into the threaded main body and Wherein the opening comprises an inner surface having inward protruding lobes and a bottom having grooves;
   a driver tool, wherein the driver tool comprises an elongated shaft, a handle attached to the proximal end of the elongated shaft and a bone fastener-engaging component attached to the distal end of the elongated shaft and wherein the bone fastener-engaging component comprises one or more structures that complement and engage at least one of the grooves and lobes of the bone fastener head opening, respectively; and
   wherein the fastener-engaging component comprises a driver and a locking sleeve and wherein the driver comprises an elongated cylindrical body having the structures at its distal end and a slot extending along the driver tool axis and wherein the cylindrical body flexes and snaps into the bone fastener opening and wherein the locking sleeve is configured to move down and lock the driver into the bone fastener head opening.

7. The assembly of claim 6, wherein the locking sleeve comprises a tubular cylindrical body and a central blade and wherein the tubular cylindrical body is dimensioned to fit and slide over the driver cylindrical elongated body and wherein the central blade is configured to be placed within the driver slot.

8. The assembly of claim 1, wherein the breakable structures comprise curved, angled or beveled outer surfaces and wherein the breakable structures outer surfaces cooperate with matching outer surfaces of the lip.

9. The assembly of claim 1, wherein the bone fastener head comprises an opening extending into the threaded main body and wherein the opening comprises pentagonal, hexagonal or octagonal geometric shape.

10. The assembly of claim 1, wherein the bone fastener head comprises an opening extending into the threaded main body and wherein the opening comprises inner threads.

11. The assembly of claim 1 wherein the elongated body comprises a first straight side surface, a second contoured side surface opposite to the first side surface, the front and back surfaces and top and bottom surfaces and wherein the elongated body further comprises one or more elongated openings configured to support bone graft material.

12. The assembly of claim 1, wherein the through-openings comprise an oval-shaped perimeter at the back surface and wherein the oval-shaped perimeter comprises two parallel straight sides and two opposite curved sides and wherein the distance between the two parallel straight sides is smaller than the major diameter of the threads of the bone fasteners and wherein the distance between the curved sides is equal to or larger than the major diameter of the threads of the bone fasteners.

13. The assembly of claim 12, wherein the bone fasteners further comprise a tapered portion extending between the threaded main body and the head and wherein the parallel straight sides of the through-openings cut into the diameter of the tapered portion for a tighter secure lock and fit.

14. The assembly of claim 1, wherein the through-openings further comprise laser-etched ridges extending perpendicular to the groove.

15. The assembly of claim 11, wherein the back surface of the cervical plate comprises a roughened texture.

16. A bone fastener comprising:
a threaded main body;
a head;
wherein the threaded main body comprises threads;
wherein the head comprises a cylindrical main body and one or more breakable structures configured to be flexed and inserted into a groove and then break and unflex upward and remain captured within the groove; and
wherein each of the one or more breakable structures comprises a curved body that extends tangentially from a first location of an outer side of the cylindrical main body and curves around a portion of the cylindrical main body and terminates to a distal end that comprises a weak breakable attachment to a second location of the outer side of the cylindrical main body;
wherein each breakable structure is initially attached to both the first and second locations of the cylindrical main body and wherein each breakable structure is configured to be flexed and inserted into the groove and then the weak breakable attachment of the distal end is configured to break away from the second location and the broken away distal end is configured to unflex upward and to remain captured within the groove.

17. A method for stabilizing two adjacent spinal vertebras, comprising:
providing a cervical plate comprising an elongated body having two or more through-openings extending from the front surface to the back surface of the elongated asymmetric body;
inserting two or more bone fasteners through the two or more through-openings, respectively, and attaching them to two or more locations in the two adjacent spinal vertebras, respectively, thereby attaching the cervical plate to the spinal vertebras;
wherein the through-openings comprise a first diameter at the front surface of the elongated body, a second diameter at the back surface of the elongated body and a third diameter in the area between the front and back surfaces of the elongated body and wherein the first diameter is smaller than the third diameter, thereby forming a lip at the top of the through-openings and wherein the third diameter is larger than the second diameter and the first diameter is larger than the second diameter, thereby forming a single continuous groove within the perimeter of the inner wall of the through-openings;
wherein the bone fasteners comprise a threaded main body and a head and wherein the threaded main body comprises threads for engaging the spinal vertebras and wherein the head comprises a cylindrical main body and one or more breakable structures;
wherein each of the one or more breakable structures comprises a curved body that extends tangentially from a first location of an outer side of the cylindrical main body and curves around a portion of the cylindrical main body and terminates to a distal end that comprises a weak breakable attachment to a second location of the outer side of the cylindrical main body;
wherein each breakable structure is initially attached to both the first and second locations of the cylindrical main body and wherein each breakable structure is configured to be flexed and inserted into the groove and then the weak breakable attachment of the distal end is configured to break away from the second location and the broken away distal end is configured to unflex upward and to remain captured within the groove.

18. The method of claim 17, wherein the diameter of the bone fastener head including the breakable structures in an unflexed position is larger than the first diameter of the through openings and wherein the breakable structures are configured to flex inward toward the outer side surface of the cylindrical main body when they come in contact with the lip while the bone fastener is rotated clock-wise to be driven into the vertebras and then the breakable structures are configured to break and detach from the second location of the outer side of the main cylindrical body and unflex upward once they are below the lip.

19. The method of claim 17, wherein the bone fastener head comprises an opening extending into the threaded main body and wherein the opening comprises an inner surface having six inward protruding lobes and a bottom having six grooves.

20. The method of claim 17, wherein the bone fasteners further comprise a tapered portion extending between the threaded main body and the head.

* * * * *